United States Patent [19]
Brannigan et al.
[11] Patent Number: 4,753,241
[45] Date of Patent: * Jun. 28, 1988

[54] METHOD OF FORMING AND USING A THERAPEUTIC DEVICE

[75] Inventors: Patrick J. Brannigan; Gerald L. Peckich, both of Pittsburgh, Pa.
[73] Assignee: Fastencold, Inc., Pittsburgh, Pa.

[ * ] Notice: The portion of the term of this patent subsequent to Mar. 11, 2003 has been disclaimed.
[21] Appl. No.: 838,518
[22] Filed: Mar. 10, 1986

Related U.S. Application Data

[63] Continuation-in-part of Ser. No. 616,489, Jun. 1, 1984, Pat. No. 4,575,097.

[51] Int. Cl.[4] .......... A61F 7/10
[52] U.S. Cl. .......... 128/380; 62/530; 128/381; 128/382; 128/384; 128/402; 156/210
[58] Field of Search .......... 128/379, 380, 381, 382, 128/384, 402, 403; 5/449; 62/530; 126/204; 165/46; 156/210

[56] References Cited

U.S. PATENT DOCUMENTS

| | | | |
|---|---|---|---|
| 1,627,523 | 5/1927 | Morris | 128/402 |
| 2,547,886 | 4/1951 | Paux . | |
| 2,562,121 | 7/1951 | Poux . | |
| 2,589,577 | 3/1952 | Rosenthal et al. | 62/530 X |
| 2,595,328 | 5/1952 | Bowen | 62/530 |
| 2,602,302 | 7/1952 | Poux | 62/530 |
| 2,648,325 | 8/1953 | Siple | 126/204 |
| 3,075,529 | 1/1963 | Young, Jr. | 128/403 |
| 3,149,943 | 9/1964 | Amador | 62/4 |
| 3,285,793 | 11/1966 | Chavannes . | |
| 3,346,438 | 10/1967 | Chavannes | 156/210 |
| 3,392,081 | 7/1968 | Chavannes . | |
| 3,405,020 | 10/1968 | Chavannes | 156/306 |
| 3,415,711 | 12/1968 | Chavannes . | |
| 3,416,984 | 12/1968 | Chavannes et al. | 156/109 |
| 3,429,315 | 2/1969 | McDonald | 128/402 |
| 3,463,161 | 8/1969 | Andrassy | 128/402 |
| 3,506,013 | 4/1970 | Zdenek | 128/402 |
| 3,508,992 | 4/1970 | Chavannes | 156/109 |
| 3,514,362 | 5/1970 | Chavannes | 156/498 |
| 3,524,787 | 8/1970 | Chavannes | 156/498 |
| 3,586,565 | 6/1971 | Fielding | 156/210 |
| 3,616,155 | 10/1971 | Chavannes . | |
| 3,785,899 | 1/1974 | Fielding | 156/209 |
| 3,868,056 | 2/1975 | Keren | 53/390 |
| 3,950,789 | 4/1976 | Konz et al. | 2/93 |
| 4,044,773 | 8/1977 | Baldwin, III | 128/402 |
| 4,074,505 | 2/1978 | Keren et al. | 53/28 |
| 4,196,160 | 4/1980 | Sperry | 264/40.4 |

*Primary Examiner*—Anton O. Oechsle
*Attorney, Agent, or Firm*—Buchanan Ingersoll

[57] ABSTRACT

A therapeutic device includes a first flexible layer having a plurality of interconnected raised chambers and passageways. The upper surface of a second flexible layer is positioned oppositely of the lower surface of the first flexible layer. The periphery of the overlying layers is heat sealed to form a plurality of chambers spaced from each other and connected by the passageways. A thermal responsive medium is introduced through the passageways into the chambers. Initially the chambers are not completely filled. Thereafter the overlying layers are further heat sealed to remove the passageways between the chambers. Consequently, the liquid that was present in the passageways is evacuated into the chambers, filling the chambers which are individually sealed from one another. For heat treatment application a third flexible layer is sealingly engaged to the lower surface of the second flexible layer and is wetted with an aqueous solution. The heated therapeutic device is then applied to the desired body portion with the cells of the flexible insulating member positioned against the body portion to be treated. The flexible nature of the therapeutic device permits the device to be compressively held in close conformity to the body portion to enhance the rate of transfer of hot or cold temperature to the effected body portion.

7 Claims, 6 Drawing Sheets

METHOD OF FORMING AND USING A THERAPEUTIC DEVICE

CROSS REFERENCE TO RELATED APPLICATION

This application is a continuation in part of U.S. application Ser. No. 616,489 filed June 1, 1984, now U.S. Pat. No. 4,575,097.

BACKGROUND OF THE INVENTION

1. Field of the Invention

This invention relates to a method for forming and using a therapeutic device and, more particularly, to a method for forming and using a therapeutic device for an anatomical body portion with a thermal responsive medium.

2. Description of the Prior Art

Various ice packs, temperature maintaining devices, body warming devices, refrigerant packages, etc. are well known to perform either a heating or a cooling function, depending upon the nature of the device and the method of use in the treatment of trauma having an inflammatory response. These devices are adaptable for heating or cooling, as the case may be, various parts of the human body. For example, U.S. Pat. No. 2,589,577 to Rosenthal et al. discloses an ice pack formed of vinyl plastic sheeting. The ice pack has a plurality of chambers into which water or other suitable liquid is introduced through successive small passageways to fill the chambers with the requisite amount of liquid. The chambers are connected by welded areas. When the ice pack is frozen, the ice must be broken in order to bend the ice pack to the desired shape.

U.S. Pat. No. 3,463,161 to Andrassy discloses a temperature maintaining device in the form of a pad which may be used for heating or cooling. The pad includes two sheets of heat sealable flexible plastic material which are heat sealed to provide a plurality of relatively small compartments having barriers with restricted passages therebetween. The compartments are filled with a temperature retaining plastic composition by working the composition through the passages. One face of the pad may desirably have a layer of thermal insulating material applied thereto to minimize heat transfer to or from the pad through the pad's exposed face.

U.S. Pat. No. 3,506,013 to Zdenek discloses a method of making an iced dressing having one or more hermetically sealed compartments which are filled with a suitable liquid, such as water. In one embodiment, a plurality of separate subcompartments are separated from each other by longitudinal and lateral hinge portions. A plurality of communicating passages connect adjacent subcompartments to facilitate filling. The communicating passages are of relatively small size so that, when filled with a frozen material, they will readily break to allow folding along the respective hinge portions.

U.S. Pat. No. 2,562,121 to Poux discloses a therapeutic device for heating or withdrawing heat from parts of the human body. A plurality of permanently sealed compartments contain liquid with air-containing cells arranged therewith. The air-containing cells function as a cushioning or insulating means for the compartments containing liquid.

U.S. Pat. No. 2,648,325 to Siple discloses a body warmer having a heated liquid circulating system that includes a plurality of flexible tubes. The tubes have enlarged compressible bulbs integral therewith. Compression and expansion of the bulbs creates a pumping action causing the liquid to circulate. The body warmer is incorporated in a jacket and the action of breathing causes the compression and expansion of the bulbs. It is also disclosed that the device can be used to cool the body.

U.S. Pat. No. 1,627,523 to Morris discloses a face mask and cap. The cap has a sealable vent with a cap element. The vent communicates with tubing for admitting water to and withdrawing water from the tube. A suitable cloth or other absorbent material can be applied under the cap next to the head of the wearer.

U.S. Pat. No. 2,547,886 to Poux discloses a therapeutic device for use as an ice or hot water bag or pack having a loose mass of permanently sealed capsule-like members having a liquid therein. The capsule-like members are disposed within a permanently sealed hollow body member or within a plurality of permanently sealed independent compartments within an elongated body member. Water is preferably used as the liquid within the permanently sealed capsule-like members.

U.S. Pat. No. 2,602,302 to Poux discloses a combination ice and hot pack having a plurality of independent and sealed fluid-containing compartments. The compartments are spaced from each other by a relatively thin, flat and wide web of material allowing flexibility.

U.S. Pat. No. 3,075,529 to Young, Jr. discloses a therapeutic heat transfer device for temperature control of a human body. In one embodiment the device has a plurality of compartments formed by longitudinal and transverse welds. The compartments are filled with a thixotropic mixture.

U.S. Pat. No. 3,149,943 to Amador discloses a chemical refrigerant package for use as an ice pack. An envelope is divided into two compartments. One compartment is filled with a dry refrigerating substance, and the other compartment is filled with water or other suitable fluid. The compartments are initially sealed from each other. When the seal is eliminated, the contents of the compartments mix, producing an endothermic chemical reaction thereby reducing the temperature of the water or other suitable fluid.

U.S. Pat. No. 3,429,315 to McDonald discloses a chemical refrigerant blanket for cooling large areas of the body. The refrigerant blanket has a plurality of elongated chambers. Each chamber is divided into two compartments, one of which contains a granular material or endothermic salt and the other compartment contains a fluid. A clamping means separates the two compartments. When the clamping means is removed, the fluid and the granular material mix, producing an endothermic reaction which reduces the temperature surrounding the blanket.

U.S. Pat. No. 3,950,789 to Konz et al. discloses a dry ice cooling jacket which provides cooling by convection as carbon dioxide gas circulates within the space between the jacket's inside surface and the body of the wearer.

U.S. Pat. No. 4,044,773 to Baldwin, III discloses a cold therapeutic package and a method of using a cold therapeutic package. In Baldwin, two sheets of polyurethane film are sealed together to provide a hollow interior which is filled with a fluid, such as water. The hollow interior is designed such that the water therein can be frozen into a thin layer which can be readily cracked and fragmented into small ice pieces. The therapeutic package having the cracked ice therein is then applied to the area to be treated.

Various cellular materials for cushioning and insulating applications are known, as well as methods and apparatus for making the cellular material. For example, U.S. Pat. No. 3,415,711 to Chavannes discloses a cushioning and insulating material formed of at least two layers of plastic material. At least one of the layers of plastic material has discrete embossments. The side walls of the embossments are fused to the side walls of adjoining embossments to provide a pair of spaced layers of plastic material with a honeycomb structure of air cells between the layers.

U.S. Pat. No. 3,346,438 to Chavannes discloses a method and apparatus for making cushioning and insulating material wherein a plurality of hermetically sealed air pockets are joined, one to another, forming a sealed honeycomb structure. In the method, a first plastic film is heated and molded to provide a plurality of closely spaced embossments. A second plastic film is heated to a fusing temperature and fed, in overlying relationship with the unembossed portions of the first film. Thus the films are fused together to form a unitary structure having a plurality of closely spaced, hermetically sealed air pockets. The embossed surface of the unitary structure is heated to the melting point of the plastic films. The heated structure is compressed to fuse the side walls of adjoining embossments to one another. The resultant cushioning material is then cooled.

U.S. Pat. Nos. 3,285,793 and 3,392,081 to Chavannes disclose a multi-laminate cushioning material having two composite layers of plastic material. At least one of the layers is embossed and the other layer is sealed to the embossed layer forming a plurality of sealed air cells.

While it is well known to use various therapeutic devices as above discussed in the treatment of inflammatory type injuries to soft tissues, including muscles, tendons, and ligaments, the known devices are limited in their effectiveness in applying either heat or cold to the affected area of the body. The principal limitations are maintaining the device in place without discomfort and conforming the device to the body part in compression.

Therefore, there is needed a therapeutic device which can adequately conform to a body portion for use in hot or cold temperature applications. The therapeutic device must promote uniform distribution of heat transfer to or from the body portion under either hot or cold temperature applications, respectively. This requires that the device apply uniform compressive forces over the body part to promote rapid heat transfer. Additionally, a therapeutic device is needed which promotes a rapid reduction or increase in body surface temperature over a relatively short time period while minimizing discomfort.

Further, a therapeutic device is needed for the application of heat treatment which promotes a substantially uniform heat transfer to the body portion while minimizing discomfort and without damaging the skin of the body portion being treated.

SUMMARY OF THE INVENTION

The present invention is directed to a method of providing moist heat treatment to a body portion. A flexible therapeutic device has a plurality of raised, outwardly projecting passageways therebetween. A thermal responsive medium is introduced into the passageways to partially fill the chambers with the medium. The chambers are sealed from one another to force the medium in the passageways into the chambers to completely fill the chambers and remove the passageways between the chambers. The flexible therapeutic device is heated to a preselected temperature. A flexible insulating member has an upper and a lower surface and a plurality of raised cells containing an insulating medium extending outwardly from the lower surface of the flexible insulating member. The flexible insulating member is moistened with an aqueous solution. The upper surface of the flexible insulating member is connected to the flexible therapeutic device with the raised cells containing the insulating medium extending outwardly from the lower surface of the flexible insulating member opposite the chambers. The flexible therapeutic device having the flexible insulating member connected therewith is positioned against the body portion to be treated with the insulating medium containing cells of the flexible insulating member positioned against the body portion to be treated. Heat transfer from the thermal responsive medium in the therapeutic device through the flexible insulating member provides moist treatment to the body portion. The aqueous solution contacts the body portion through the moistened insulating member.

The present invention additionally provides a method for forming a therapeutic device which includes a first flexible layer having an upper and a lower surface. The upper surface includes a plurality of raised, chamber-like projections and raised channel-like portions which connect pairs of adjacent chamber-like projections. A second flexible layer is provided having an upper and a lower surface. The lower surface of the first flexible layer is sealingly engaged to the upper surface of the second flexible layer to thereby form the plurality of chambers spaced from each other with adjacent chambers being connected by the raised, channel-like portions forming passageways therebetween. A thermal responsive medium is introduced with the chambers and the passageways. The portions of the first and second flexible layers forming the passageways between the chambers are sealed to remove the passageways between the chambers and provide a plurality of discrete chambers separated from one another and containing said thermal responsive medium.

An object of the present invention is to provide a method for providing moist heat treatment which promotes substantially uniform heat transfer to the body portion being treated.

Another object of the present invention is to provide a method for forming a therapeutic device which promotes ease of assembly and facilitates filing the therapeutic device with a thermal responsive medium.

These and other objects of the present invention will be more completely disclosed and described in the following specification, the accompanying drawings, and the appended claims.

Figure 1:
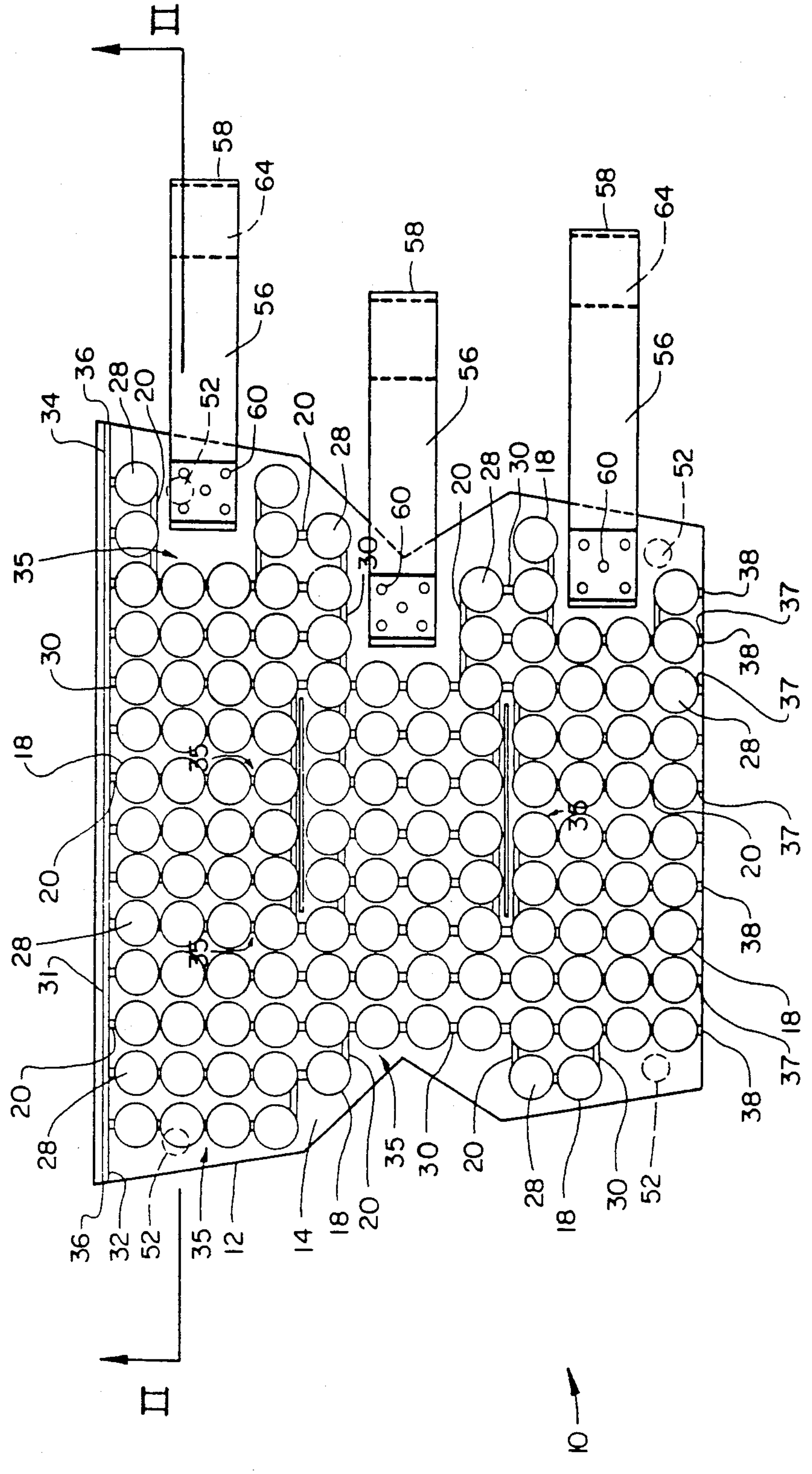
FIG. 1 is a plane view of one embodiment of a therapeutic device in accordance with the present invention.
Figure 4:
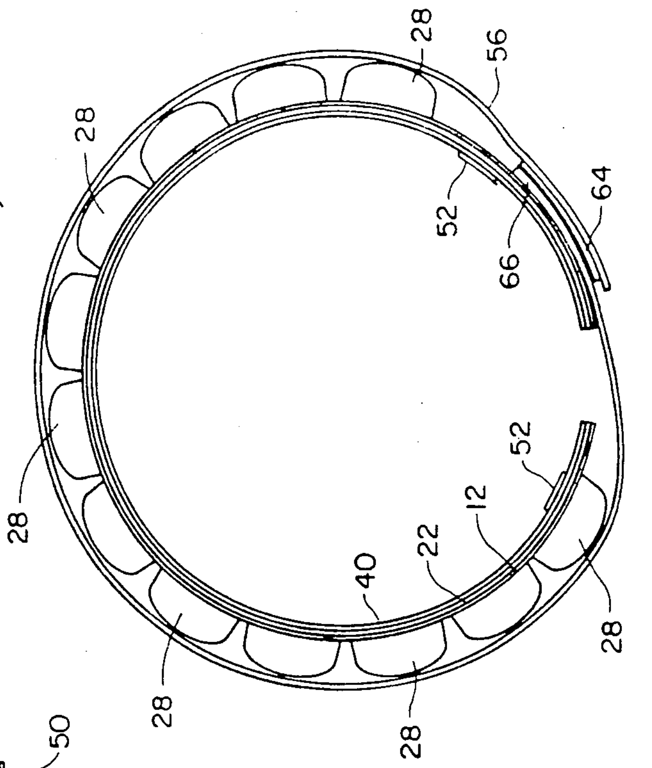

FIG. 4 is a side view of the therapeutic device of FIG. 1, illustrating fastening of the therapeutic device around a body part.

Figure 2:
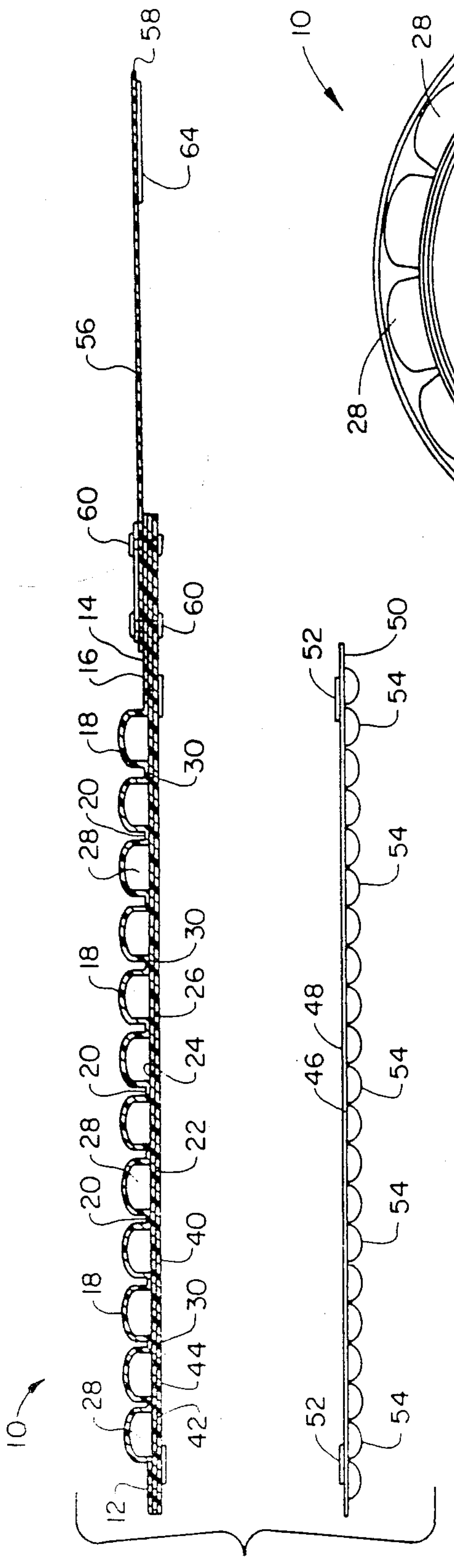
FIG. 2 is an exploded, sectional view, taken along line II—II of FIG. 1, illustrating the removable connection of a flexible insulating member to the therapeutic device.
Figure 5:
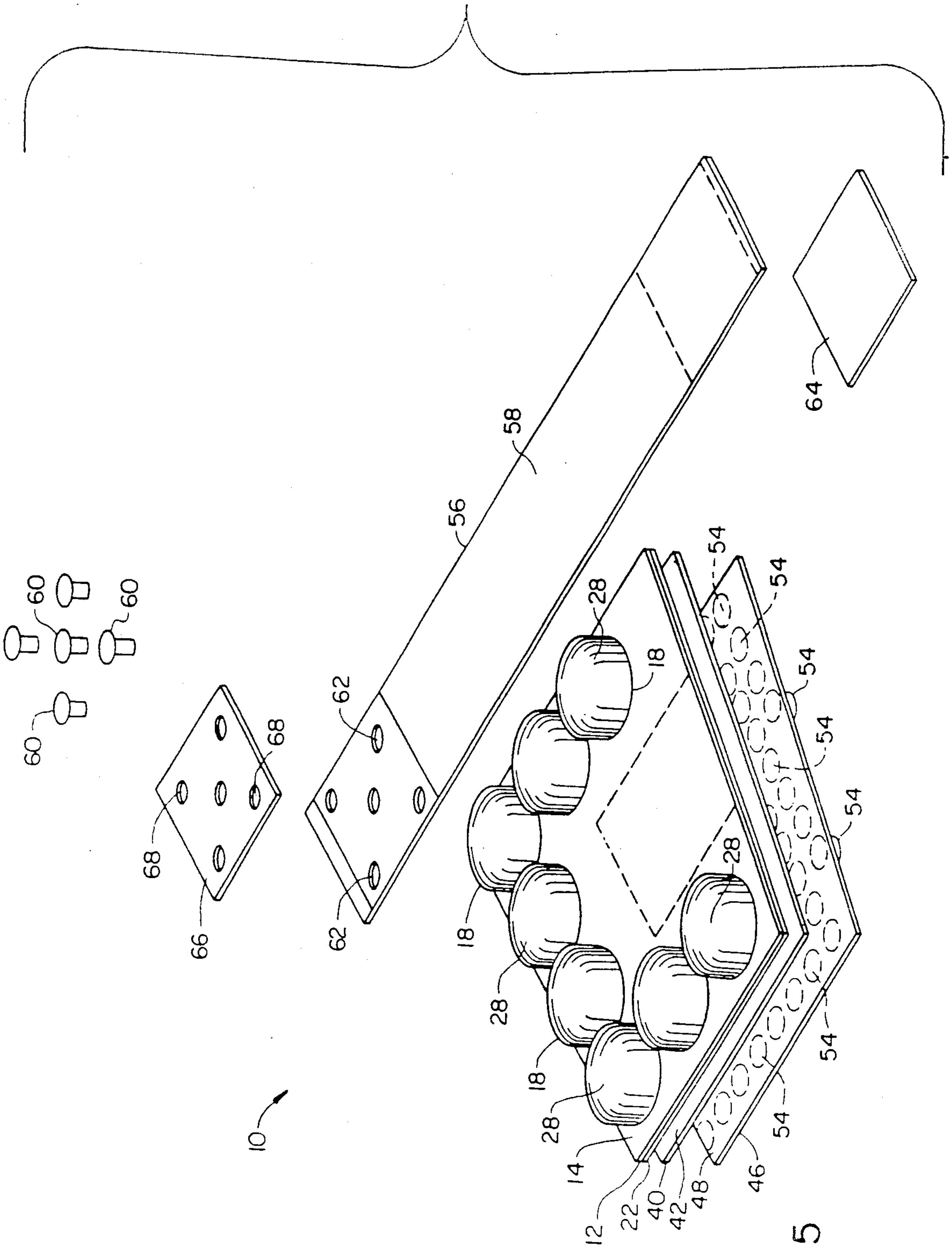

FIG. 5 is an exploded, fragmentary, isometric view of a portion of the therapeutic device of FIGS. 1 and 2, illustrating the various flexible layers and a flexible insulating member, as well as showing means for fastening the therapeutic device to a body portion.

Figure 6:
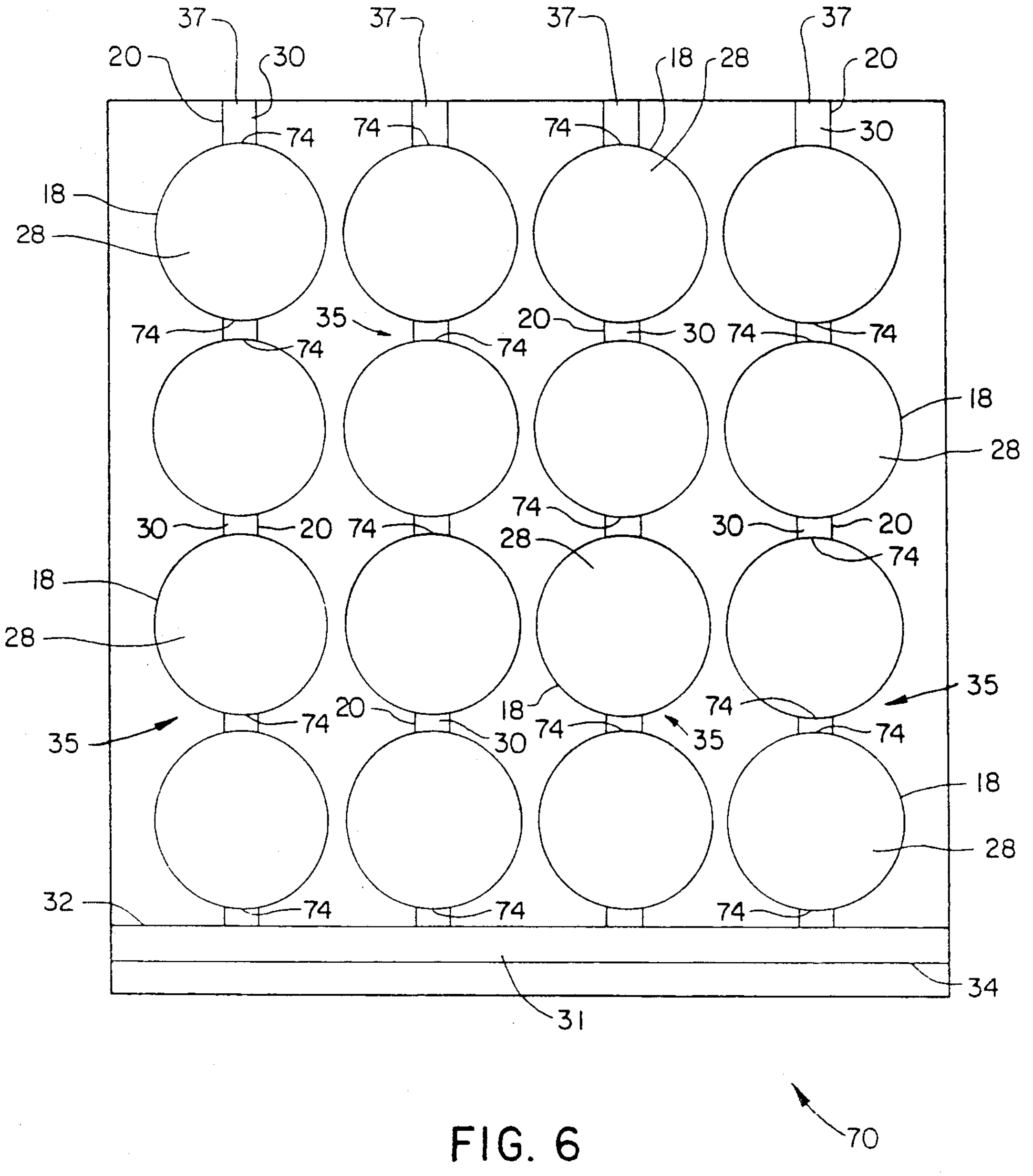

FIG. 6 is a fragmentary, plane view showing a portion of another embodiment of the therapeutic device of the present invention, illustrating sealing of the passageways to provide discrete chambers.

Figure 7:
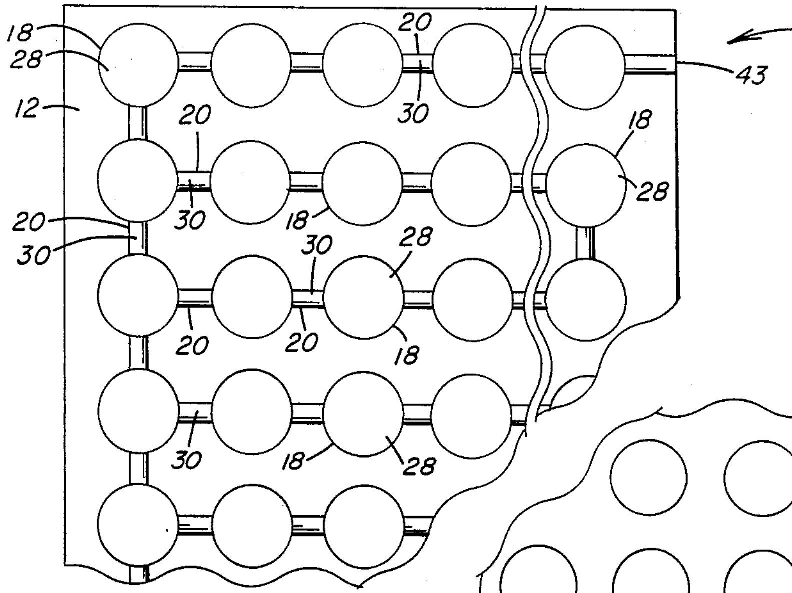

FIG. 7 is a view similar to FIG. 6, illustrating another embodiment of the therapeutic device in which the chambers are connected by the passageways prior to sealing of the chambers after filling with a thermal responsive medium.

Figure 8:
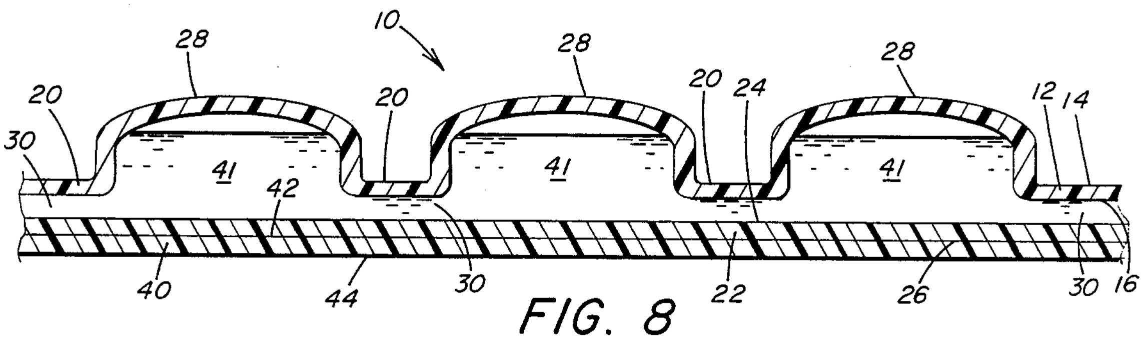

FIG. 8 is an enlarged fragmentary, sectional view of the therapeutic device shown in FIG. 7.

Figure 9:
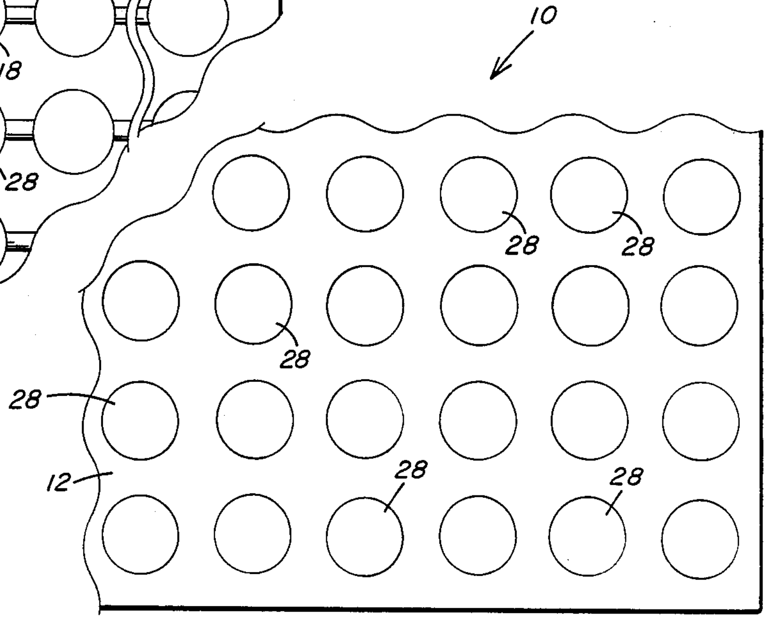

FIG. 9 is a view similar to FIG. 7, illustrating the chambers sealed from one another and the connecting passageways removed.

Figure 10:
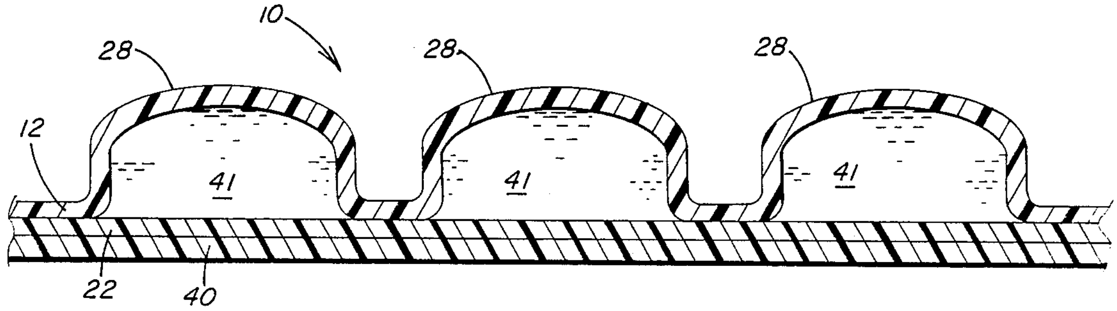

FIG. 10 is a view similar to FIG. 8, illustrating the step of sealing the chambers one from another thereby completely filling the chambers with the medium present in the passageways which have been removed by the sealing.

Figures 11, 12:
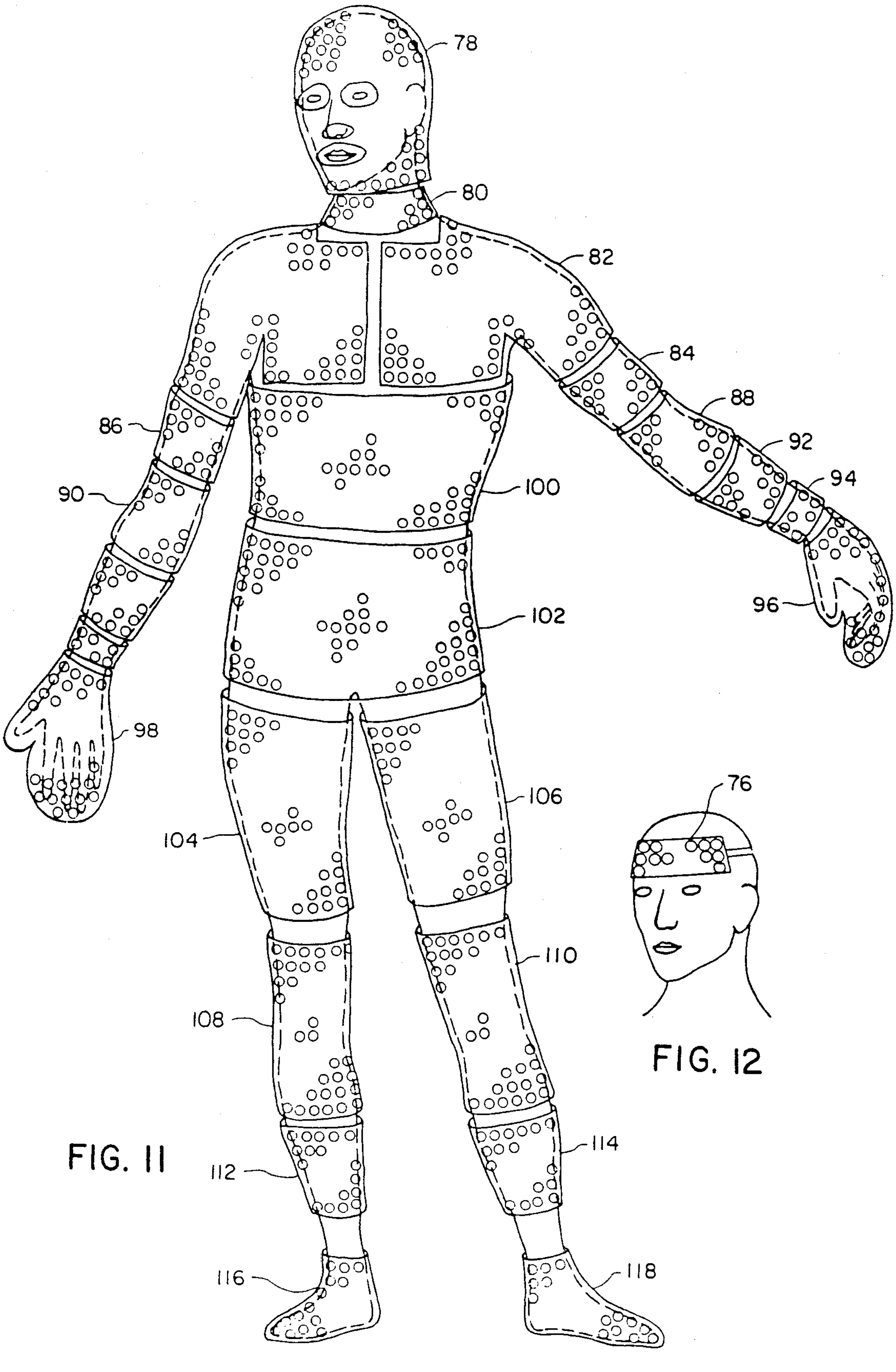

FIG. 11 is a schematic anatomical view, illustrating various therapeutic devices of the present invention for covering the entire human anatomy in therapeutic treatment.

FIG. 12 is a fragmentary schematic view, illustrating a therapeutic device of the present invention being applied to the forehead region of the human body.

DESCRIPTION OF THE PREFERRED EMBODIMENTS

Figure 3:
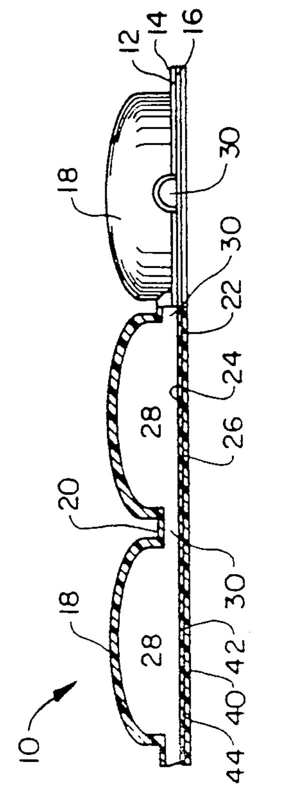
FIG. 3 is an enlarged fragmentary, sectional view of a portion of the therapeutic device shown in FIGS. 1 and 2, illustrating the chambers and the interconnecting passageways therebetween.

Referring to the drawings and particularly to FIGS. 1–5, there is illustrated a therapeutic device generally designated by the numeral 10 that includes a first flexible layer 12 having an upper surface 14 and a lower surface 16. The first flexible layer 12 includes a plurality of raised chamber-like projections 18 and a plurality of raised channel-like portions 20, as shown in FIGS. 2 and 3. The raised channel-like portions 20 interconnect pairs of adjacent chamber-like projections 18. First flexible layer 12 is formed from a sheet of a suitable flexible material, such as polyethylene or other appropriate plastic material and may be a composite material. It is desirable that first flexible layer 12 have a thickness in the range of about 4–12 mls.

Therapeutic device 10 further includes a second flexible layer 22 including an upper surface 24 and a lower surface 26. The upper surface 24 of second flexible layer 22 is sealingly engaged to lower surface 16 of first flexible layer 12 to thereby form a plurality of chambers 28 spaced from each other with adjacent chambers 28 being connected by the raised channel-like portions 20 to form passageways 30 therebetween. The sealing engagement of the upper surface 24 of second flexible layer 22 to the lower surface 16 of first flexible layer 12 is accomplished by any conventionally known means, such as by heat sealing with any of various conventional heat sealing apparatus. Second flexible layer 22 is formed from a sheet of a suitable flexible material, such as polyethylene or an appropriate plastic material and may be a composite material. Second flexible layer 22 desirably has a thickness in the range of about 4–12 mls.

Chambers 28 and passageways 30 are adapted to be filled with a thermal responsive medium, such as water or a copper sulfate solution. The thermal responsive medium occupies the chambers 28 and passageways 30 when the therapeutic device 10 is in use. Any of a suitable number of thermal responsible mediums can be employed. It is preferable that the thermal responsive medium be chosen so as to have applicability over a wide temperature range, such as for hot or cold temperature application. A thermal responsive medium can be selected for a specific hot or cold temperature application in those cases when the therapeutic device 10 is used exclusively for a hot or a cold temperature application. The thermal responsive medium is heated or cooled, depending upon whether the therapeutic device 10 is to be used for hot or cold temperature applications.

It is preferred that a substantial portion of chambers 28 and passageways 30 be serially connected with each other by a manifold-type system, as shown in FIG. 1. The serial connection of chambers 28 and passageways 30 facilitates efficient filling of the chambers 28 and passageways 30 with the thermal responsive medium and obviates the need to fill each chamber and passageway individually. This arrangement promotes a substantial time savings in the filling of therapeutic device 10.

As shown in FIG. 1, therapeutic device 10 includes a manifold 31 having inlets 32 and 34. The manifold 31 can be of any suitable configuration depending upon the particular needs involved in filling chambers 28 and passageways 30. For example, manifold 31 has a channel-like configuration communicating with a plurality of banks 35 of chambers 28 connected in series by passageways 30. The banks 35 are vertically arranged and extend the length of the device. Each bank 35 of connected chambers 28 includes an outlet 37. Thus a continuous fluid circuit is informed to facilitate filling of the chambers 28 and passageways 30 from the manifold 31 with the thermal responsive medium. This arrangement promotes an even distribution of the thermal responsive medium in the chambers and passageways.

Once the chambers 28 and passageways 30 are filled with a thermal responsive medium, in accordance with one method of the present invention, the inlets 32 and 34 and outlets 37 are sealed to prevent flow of the thermal responsive medium out of the chambers 28. A variety of sealing means can be employed, such as conventional heat sealing machinery to close the inlets 32 and 34, and outlets 37 by the seals 36 and 38 shown in FIG. 1. In a second method of operation as shown in FIGS. 7–10, in which like numerals refer to like parts in FIGS. 1–6, the passageways connecting the chambers 28 are removed during the operation of sealing the chambers 28 from each other. The medium previously occupying the passageways 30 is evacuated into the chambers 28 upon their sealing. In this manner, planar areas are formed between chambers 28 by fusing together the opposite surfaces of the flexible layers 12 and 22 during the sealing of the chambers 28.

Chambers 28 and passageways 30 can be of any suitable configuration, circular, square, diamond shaped, etc., depending upon the particular use and application. It is desirable that chambers 28 have a generally domed, semi-cylindrical configuration as shown in FIGS. 3, 4, and 5. Also, to provide flexibility to therapeutic device 10 for ease in conforming therapeutic device 10 to a body portion, chambers 28 are spaced a preselected distance from each other. Further, it is desirable that passageways 30 have a generally semi-cylindrical configuration as shown in FIG. 3. The size and dimensions of chambers 28 and passageways 30 can vary, depending upon the particular use and application for therapeutic device 10. However, it is desirable that passageways 30 be of a relatively smaller size than chambers 28, as shown in FIG. 3, to facilitate conforming therapeutic device 10 to a body portion, particularly for cold temperature applications where the thermal responsive medium is initially in a frozen state.

Further in accordance with the present invention there is provided a third flexible layer 40 as shown in FIGS. 2-5. Third flexible layer 40 has an upper surface 42 and a lower surface 44. When third flexible layer 40 is employed with therapeutic device 10, upper surface 42 of third flexible layer 40 is sealingly engaged to the lower surface 26 of second flexible layer 22. Use of a third flexible layer 40 provides an insulation barrier between the body portion and therapeutic device 10 when therapeutic device 10 is used for cold temperature applications.

Third flexible layer 40 is sealingly engaged to second flexible layer 22, as mentioned above, by any number of suitable conventional means, such as by heat sealing third flexible layer 40 to second flexible layer 22 using conventional heat sealing machinery. Third flexible layer 40 is formed from a sheet of any suitable flexible material, such as polyethylene or other appropriate plastic material and may be a composite material. Preferably the third flexible layer 40 has a thickness in the range of about 4–12 mls.

When used for hot temperature applications, therapeutic device 10 has a flexible insulating member 46 connected therewith, as shown in FIGS. 2 and 5. Flexible insulating member 46 may be used for certain cold temperature applications, if desired. Flexible insulating member 46 has an upper surface 48 and a lower surface 50. Preferably the flexible insulating member 46 is removably connected to the lower surface 44 of third flexible layer 40.

The removable connection of flexible insulating member 46 with third flexible layer 40 is formed by a plurality of pressure sensitive hook and loop fasteners 52 positioned on the lower surface 44 of third flexible layer 40 and on the upper surface 48 of flexible insulating member 46. The hook portion of the hook and loop fastener 52 is provided on either the upper surface 48 of flexible insulating member 46 or on the lower surface 44 of third flexible layer 40. The fastener portion of hook and loop fastener 52 is positioned opposite the hook portion on either lower surface 44 or upper surface 48, respectively, as the case may be. The hook and loop fasteners 52 are shown in FIGS. 1, 2, and 4.

Preferably the hook and loop fasteners 52 are pressure sensitive woven nylon hook and loop fasteners, commercially known as VELCRO. The size and dimensions of the hook and loop fasteners 52 can vary, depending upon the use and application. Preferably the hook and loop fasteners 52 have a generally circular disk-like shape in which the diameter of the generally circular disk-like shape hook and loop fasteners is about ½ inch.

Flexible insulating member 46, as shown in FIGS. 2 and 5, has a plurality of raised cells 54 extending outwardly from lower surface 50 of flexible insulating member 46. Raised cells 54 contain an insulating medium, generally air, but other suitable insulating mediums can be employed. The raised cells 54 are sealed from each other, such as by a conventional heat seal, and are spaced from one another to provide flexibility of the insulating member 46.

Preferably flexible insulating member 46 is formed from two sheets of a suitable flexible material, such as polyethylene or other appropriate plastic material and may be a composite material. The sheets are heat sealed together and the raised cells are formed by conventional apparatus for manufacturing cellular material. When therapeutic device 10 is used with flexible insulating member 46, the insulating medium containing raised cells 54 is positioned against the body portion to be treated.

Referring to FIGS. 1, 2, 4 and 5, there is illustrated fasteners 56 for fastening therapeutic device 10 to a body portion. The fasteners 56 have a flexible, elastic strap portion 58 formed of a suitable elastic material. At least one grommet-like connector 60 is provided to connect the elastic strap portion 58 to at least one of the flexible layers of therapeutic device 10. In the therapeutic device 10 shown in FIG. 1, a plurality of grommet-like connectors 60 connect each elastic strap portion 58 to the flexible layers 12, 22 and 40.

Suitably sized openings 62 are provided in elastic strap portion 58 for the grommet-like connectors 60, as shown in FIG. 5. A pressure sensitive hook 64 and loop 66 fastener is suitably attached to each flexible, elastic strap portion 58. The loop 66 of the hook and loop fastener is attached to elastic strap portion 58 by the grommet-like connectors 60 passing through openings 68 in loop 66. Hook 64 is suitably attached to elastic strap portion 58 in a conventional manner. Fastening hook 64 with the respective loop 66 of the hook and loop fastener as shown in FIG. 4 secures the therapeutic device 10 to the body portion to be treated.

Use of suitable fasteners, such as body portion fasteners 56, are preferred when securing therapeutic device 10 to various body portions, such as to arm or leg portions. The body portion fastener 56 described herein is an example of one type of fastener which can be used with therapeutic device 10. Other suitable fasteners can be utilized depending upon the application. Most preferably body portion fastener 56, hook 64 and loop 66 are pressure sensitive woven nylon hook and loop fasteners.

Referring to FIG. 6, there is illustrated a portion of a therapeutic device 70, similar to the therapeutic device 10 shown in FIGS. 1–5. The numerals used to designate the elements of therapeutic device 70 correspond to the numerals used to designate like elements of therapeutic device 10. Therapeutic device 70 has a plurality of chambers 28 interconnected by passageways 30. As can be seen in FIG. 6, a substantial portion of chambers 28 and passageways 30 are serially connected to each other. Therapeutic device 70 has a manifold 31 connected to serially connected banks 35 of chambers 28. The manifold 31 has inlets 32 and 34.

After chambers 28 and passageways 30 are filled with a thermal responsive medium such as water, the passageways 30 are sealed to provide discrete chambers 28 containing the thermal responsive medium. A heat seal 74 is desirably applied at the intersection of each passageway 30 with the respective chambers 28. Thus the passageways 30 are sealed from the chamber 28 to provide discrete chambers containing the thermal responsive medium.

Heat seal 74 can be formed in a conventional manner by suitable heat sealing machinery. Other suitable means to seal may be employed, depending upon the particular use and application. In operation the passageways 30 are sealed to provide discrete chambers 28 after the passageways 30 and chambers 28 have been filled with a thermal responsive medium. With this arrangement, if one or more chambers 28 or passageways 30 rupture, the remaining chambers 28 and passageways 30 remain intact and their thermal responsive medium is not lost. Heat seals 74 can also be utilized with therapeutic device 10 of FIG. 1 to provide discrete chambers 28 containing a thermal responsive medium.

In accordance with the method of the present invention for forming therapeutic device 10, first flexible layer 12 including a plurality of raised chamber-like projections 18 and raised channel-like portions 20 is formed by conventional apparatus having a suitable embossing roller or rollers designed to provide the appropriate configuration for the chamber-like projections 18 and channel-like portions 20. The lower surface 16 of first flexible layer 12 is sealingly engaged to the upper surface 24 of second flexible layer 22 to thereby form a plurality of chambers 28 spaced from each other with adjacent chambers 28 being connected by raised channel-like portions 20 forming passageway 30 therebetween.

The sealing engagement of the second flexible layer 22 to the first flexible layer 12 is accomplished, for example, by heat sealing the layers together using conventionally known apparatus for the manufacture of various cellular materials. A thermal responsive medium is provided within the chamber 28 and passageway 30. This is accomplished, for example, by injecting at either one of the manifold inlets 32 or 34 the thermal responsive medium into a suitable passageway or passageways 30 of the interconnected chambers 28 and passageways 30. Once the chambers 28 and passageways 30 are filled, the manifold inlets 32 and 34 and the outlets 37 are heat sealed.

In one method for forming the therapeutic device 10, it is desirable to provide an inlet means, such as inlets 32 and 34, and an outlet means, such as outlets 34 shown in FIG. 1. The inlets 32 and 34 are connected by the manifold 31 and the banks 35 of serially connected chambers 28 to the outlets 37. As shown in FIG. 1, each of the chambers 28 in the respective banks 35 are serially connected by the passageways 30. With this arrangement all the chambers 28 and passageways 30 are filled from the inlets 32 and 34. This structure is fabricated by use of conventional apparatus for the manufacture of cellular material having a suitable embossing roller or rollers to provide the above described inlets 32 and 34 and outlets 37, as well as the interconnection of the manifold 31 and banks 37 with the inlets 32 and 34, chambers 28, passageways 30, and outlets 37. The sealing of the inlets 32 and 34 and the outlets 37 is accomplished by conventionally known heat sealing machinery through application of heat seals 36 and 38 to the inlets 32 and 34 and outlets 37, respectively.

In another method of forming a therapeutic device of the present invention, a third flexible layer 40, as previously discussed herein, sealingly engages the lower surface 26 of the second flexible layer 22 to the upper surface 42 of the third flexible layer 40. Sealingly engaging the second flexible layer 22 to the third flexible layer 40 is also accomplished by heat sealing using a conventional apparatus for manufacturing of cellular material having a suitable heat sealing capability.

In forming the embodiment of the therapeutic device 10 shown in FIG. 5, the flexible insulating member 46 having an upper surface 48 and a lower surface 50 includes a plurality of raised cells 54 containing an insulating medium, such as air, extending outwardly therefrom is fabricated using conventional apparatus for the manufacture of cellular material having a suitable embossing roller or rollers to provide the raised cell construction. The flexible insulating member 46 includes at least two sheets of a flexible plastic material. The upper surface 48 of flexible insulating member 46 is removably connected to the lower surface 44 of third flexible layer 40 by a plurality of hook and loop fasteners 52, as shown in FIG. 2.

Referring to FIGS. 7–10 there is illustrated the method and apparatus by which the therapeutic device 10 is constructed without the presence of the passageways 30 connecting adjacent chambers 28 after the chambers 28 are sealed from one another. The device 10 is initially formed as above described by the composite layers 12, 22, and 40 of flexible material. The layer 12 includes the raised channel-like portions 20 extending between the adjacent chambers 28. The layer 12 is initially secured to the layer 22 by heat sealing around the perimeter of the two overlying layers. Layer 40 is heat sealed in abutting relation to the lower surface 26 of layer 22. Thus, the passageways 30, shown in FIG. 7, are formed in fluid communication with the chambers 28.

Thereafter as illustrated in FIG. 8 a thermal responsive medium 41 is introduced through an open inlet 43 into the passageways 30. A selected volume of medium is introduced for partial filling of the chambers 28. As shown in FIG. 8, the chambers 28 are initially substantially filled but not completely filled. At this point, the layer 12 is completely sealed to the layer 22 by securing in sealing engagement the portions of layer 12 having the raised channel-like portions 20 into engagement with the upper surface 24 of the second flexible layer 22. This operation removes the passageways 30 from the surface of the therapeutic device 10 as shown in FIGS. 9 and 10.

The final step of heat sealing layers 12 and 22 evacuates the fluid medium from the passageways 30 into the chambers 28, thereby filling the chambers 28, as shown in FIG. 10. The effect is to separate the filled chambers 28 one from another by planar surfaces formed by the sealed and abutting opposite surfaces of layers 12 and 22. Between and around each chamber the layer surface 16 abuts the layer surface 24. The therapeutic device 10 formed in this manner has increased flexibility, particularly in cold applications, for movement into close conformity with the body part on which it is applied for therapy. The filled chambers 28 are isolated from one another and rupture of one chamber will not affect the others.

Further in accordance with the present invention, there is provided a method for moist heat treatment to a body portion using a therapeutic device 10. To carry out this method the flexible therapeutic device 10, without having flexible insulating member 46 yet connected thereto is heated to a preselected temperature to heat the thermal responsive medium in chamber 28. Such heating can be accomplished in a microwave oven, or other suitable conventional heating means. If heating is accomplished in a microwave oven, the materials of which therapeutic device 10 are composed would be non-metallic in nature.

Once the therapeutic device 10 is heated, the flexible insulating member 46 is attached to the device 10. The flexible insulating member 46 has an upper surface 48 and a lower surface 50. A plurality of raised cells 54 containing an insulating medium, such as air, extends outwardly from the lower surface 50. The flexible insulating member 46 is moistened with an aqueous solution, such as water, before it is attached to the therapeutic device 10. The upper surface 48 of the flexible insulating member 46 is then connected to therapeutic device 10 with the raised cells 54 containing an insulating medium extending outwardly from the lower surface 50 of the flexible insulating member 46 opposite the chambers 28. The connection is made through the hook and loop fasteners 52 shown in FIG. 2.

The therapeutic device 10 having flexible insulating member 46 connected thereto is then positioned against the body portion to be treated with the insulating medium containing cells 54 of flexible insulating member 46 positioned against the body portion. In this manner moist heat treatment is applied to the body portion by heat transfer from the heated thermal responsive medium in the therapeutic device 10 through the flexible insulating member 46 to the body portion. The aqueous solution contacts the body portion through the moistened flexible insulating member 46.

The moist heat delivered to the body portion is achieved by distributing the water or other suitable aqueous solution on the raised cells 54. The water or other aqueous solution used in the moist heat treatment is distributed throughout and encaptured within and on the raised cells 54. Upon application of the cells 54 against the body portion, a direct transfer of water or other suitable aqueous solution to the body portion occurs.

Preferably, the therapeutic device 10 is heated to the desired preselected temperature without the flexible insulating member 46. Then the flexible insulating member 46 is attached to device 10. However in certain cases and for certain applications the therapeutic device 10 and the insulating member 46 connected thereto are heated together. Further, for certain moist heat applications to various body portions, such as various arm portions or leg portions of the human body, it is desirable to fasten the therapeutic device 10 with the flexible insulating member 46 connected thereto to the body portion. The fastening of the therapeutic device 10 to the body portion is accomplished by the body portion fasteners 56, as discussed above.

The method for providing moist heat treatment to a body portion, as previously described, promotes substantially uniform heat transfer to the body portion being treated. It also promotes transfer of the water or other suitable aqueous solution used in the moist heat treatment to the body portion. With this method of heat treatment there is no discomfort or damage to the skin of the body portion being treated. This is particularly advantageous when applying moist heat treatment to a body portion for an extended period, such as approximately 30 minutes to prevent any discomfort which may otherwise occur. By use of the flexible insulating member 46 with the therapeutic device 10 of the present invention, the thermal responsive medium, typically being water, can be heated to a boiling temperature prior to application to the body portion.

For various cold temperature applications, the therapeutic device 10 is cooled in a suitable refrigeration device, such as in a refrigerator or freezer, or surrounded with ice or dry ice. The thermal responsive medium is cooled to a preselected temperature or is frozen, if necessary. If the thermal responsive medium is frozen, then the plurality of passageways 30 between chambers 28 allows the therapeutic device 10 to easily conform to the body portion to be treated during the cold temperature application.

By the therapeutic device 10 conforming to the body portion, compression is applied to the body portion when the device 10 is securely fastened around and in contact with the body portion. Compression aids in the transfer of heat or cold to the body portion. If the thermal responsive medium is frozen for a cold temperature application of therapeutic device 10, cracking or breaking of the frozen thermal responsive medium in the passageways 30 facilitates flexibility and conformance of therapeutic device 10 to the body portion to be treated.

With the therapeutic device 10 not only is the affected body portion heat treated cold or hot, but the areas surrounding the affected body portion are also treated. Particularly in ice treatment of hematoma, the therapeutic device 10 in a frozen state and compressed on the hematoma controls the swelling and promotes a decrease in blood circulation in the uninjured area of the body portion surrounding the hematoma. By decreasing the blood circulation, the cellular metabolism of the affected and surrounding area is lowered. Consequently the uninjured cells can survive the effects of hypoxy brought on by the swelling and will not die. When this occurs less tissue in the area surrounding the hematoma is injured, and the hematoma is prevented from increasing in size. By conforming in compressed relation to the injured body portion, the therapeutic device 10 effectively controls the swelling and promotes repair of the injured body portion.

A further advantage of a therapeutic device 10 is the promotion of a rapid decrease or increase in surface body temperature over a relatively short time period with no discomfort associated therewith. A cold temperature study and a hot temperature study were conducted using the therapeutic device 10 of the present invention. The therapeutic device was applied to the forearm of a human body. The results of these studies are presented in Tables 1 and 2 below.

TABLE 1

| Therapeutic Device: Cold Temperature Study | |
|---|---|
| Average time of test | 30 minutes |
| Number of participants | 13 |
| Average surface body temperature prior to testing | 85.1° F. |
| Average surface body temperature after testing | 66.5° F. |
| Average surface body temperature difference | 18.6° F. decrease in temperature |

TABLE 2

| Therapeutic Device: Hot Temperature Study | |
|---|---|
| Average time of test | 30 minutes |
| Number of participants | 13 |
| Average surface body temperature prior to testing | 87.6° F. |
| Average surface body temperature after testing | 108.2° F. |
| Average surface body temperature | 20.6° F. increase in |

TABLE 2-continued

| Therapeutic Device: Hot Temperature Study | |
| --- | --- |
| difference | temperature |

The cold temperature study indicated that the surface body temperature could be reduced from 85.1° F. to about 66.5° F. in approximately 30 minutes without discomfort using the therapeutic device 10. Likewise, in a period of approximately 30 minutes, the surface body temperature was increased from about 87.6° F. to about 108.2° F. without discomfort through use of the flexible insulating member 46 attached to the therapeutic device 10.

Prior to the therapeutic device 10 of the present invention, providing the rate of temperature increase or decrease for the period of time as shown in Tables 1 or 2, respectively, would result in substantial discomfort to the individual. However, use of the therapeutic device 10 produces this temperature increase or decrease for the above-mentioned time period without discomfort to the person. Further, the substantially uniform heat transfer to or from the body portion, as the case may be, provided by the therapeutic device 10 minimizes or eliminates damage to the skin of the body portion being treated during either a hot or a cold temperature application.

Referring to FIGS. 11 and 12, various therapeutic devices of the present invention are shown therein being applied to various exterior portions of the human anatomy. Although the shapes and configurations of the various therapeutic devices differ, they conform to the therapeutic device 10 described above and illustrated in FIGS. 1-5, 6 or 7-10. The various therapeutic devices in FIGS. 11 and 12 will be enumerated for exemplary purpose to illustrate the versatility of the therapeutic device 10.

For example, in FIG. 12 a therapeutic device 76 is applied to the forehead of an individual. The device 76 is particularly effective in a cooled or frozen state to provide overall cooling of the body when exercising strenuously, for example running. Cooling of the forehead in this manner serves to prevent the entire body from overheating.

In FIG. 11, a plurality of therapeutic devices are shown for each part of the human anatomy to illustrate the versatility of the present invention. A therapeutic device 78 covers the entire head of an individual with the exception of openings for the eyes, nose and mouth. A therapeutic device 80 is positioned around the neck region. A therapeutic device 82 covers the shoulder area. Therapeutic devices 84, 86, 88, 90, 92 and 94 cover various portions of the arms. Therapeutic devices 96 and 98 cover the hands. Therapeutic device 100 covers the chest area or upper torso area. Therapeutic device 102 covers the waist and hip area. Therapeutic devices 104 and 106 cover the right and left thigh areas. Therapeutic devices 108 and 110 cover the right and left knee areas. Therapeutic devices 112 and 114 cover the right and left calf areas of the legs. Therapeutic devices 116 and 118 cover the right and left ankle and foot areas.

As can be seen, a plurality of configurations, shapes and sizes of the therapeutic device of the present invention are provided for all areas of the human anatomy. The therapeutic devices shown in FIG. 11 or 12 can be used for either hot or cold temperature application. When used for hot temperature application, use of the flexible insulating member 46 is preferred and connected to the therapeutic device in the manner as above described.

Additionally, the therapeutic device of the present invention can be used for hot or cold temperature applications for various portions of the bodies of animals. Also, the therapeutic device including the first and second flexible layers, as previously described herein, has added versatility in that it is adapted for use as a ground cloth in camping or as an exercise pad for aerobics. Also, the therapeutic device of the present invention can be used to alleviate pain and reduction of swelling to a body portion which has received an insect bite.

In summary, a therapeutic device of the present invention provides a superior device over known therapeutic devices in its flexibility to conform to various body portions, especially when the thermal responsive medium is in a frozen state. In use the therapeutic device promotes rapid reduction in or increase in surface body temperature over a relatively short period of time without discomfort or damage to the skin of the body portion being treated. Also, the method for providing moist heat treatment to a body portion promotes a substantially uniform heat transfer to the body portion and promotes transfer of the aqueous solution used in the moist heat treatment to the body portion being treated. This occurs without discomfort or damage to the skin area of the body portion being treated. Additionally, the method for forming a therapeutic device of the present invention promotes ease of assembly and facilitates filling of the therapeutic device with a thermal responsive medium through the interconnection of the chambers and passageways in the therapeutic device.

According to the provisions of the patent statutes, we have explained the principle, preferred construction and mode of operation of our invention and have illustrated and described what we now consider to represent its best embodiments. However, it should be understood that, within the scope of the appended claims, the invention may be practiced otherwise than as specifically illustrated and described.

We claim:

1. A method for providing moist heat treatment to a body portion comprising the steps of, providing a flexible therapeutic device having a plurality of raised, outwardly projecting chambers spaced from one another with adjacent chambers having raised, outwardly projecting passageways therebetween, introducing a thermal responsive medium into said passageways to partially fill said chambers with said medium, sealing said chambers from one another to force said medium in said passageways into said chambers to completely fill said chambers and remove said passageways between said chambers, heating said flexible therapeutic device to a preselected temperature, providing a flexible insulating member having an upper surface and a lower surface, said flexible insulating member having a plurality of raised, cells containing an insulating medium extending outwardly from said lower surface of said flexible insulating member, moistening said flexible insulating member with an aqueous solution, connecting said upper surface of said flexible insulating member to said therapeutic device with said raised cells containing an insulating medium extending outwardly from said lower surface of said flexible insulating member opposite said chambers, positioning said therapeutic device having said flexible insulating member connected thereto against a body portion to be treated with said insulating medium containing cells of said flexible insulating member being against the body portion, and transferring heat from said thermal responsive medium in said therapeutic device through said flexible insulating member to said body portion with said aqueous solution contacting said body portion through said raised cells to provide moist heat treatment of the body portion.

2. A method for providing moist heat treatment as set forth in claim 1 which includes, removing said passageways, filled with said thermal responsive medium between said chambers, and directing said thermal responsive medium from said passageways into said chambers.

3. A method for providing moist heat treatment as set forth in claim 1 which includes, providing flexible planar surfaces between said chambers.

4. A method for forming a therapeutic device comprising the steps of, providing a first flexible layer with an upper surface and a lower surface and having a plurality of raised chamber-like projections and raised channel-like portions interconnecting pairs of adjacent raised chamber-like projections, providing a second flexible layer having an upper surface and a lower surface, sealingly engaging said lower surface of said first flexible layer to said upper surface of said second flexible layer to thereby form a plurality of chambers spaced from each other with adjacent chambers being connected by said raised channel-like portions forming passageways therebetween.

introducing a thermal responsive medium through said passageways to partially fill said chambers, and sealing together the portions of said first and second flexible layers forming said passageways between said chambers to remove said passageways between said chambers and transfer said thermal responsive medium from said passageways to said chambers to provide a plurality of discrete chambers separated from one another and containing said thermal responsive medium.

5. A method for forming a therapeutic device as set forth in claim 4 which includes, evacuating said thermal responsive medium from said passageways into said chambers upon removal of said passageways between said chambers.

6. A method for forming a therapeutic device as set forth in claim 4 which includes, initially supplying said thermal responsive medium to said chambers to a preselected volume less than the entire volume of said chambers, evacuating said thermal responsive medium from said passageways into said chambers to fill said chambers upon sealing of said chambers, and removing said thermal responsive medium between said chambers so as to confine said medium to said chambers.

7. A method for forming a therapeutic device as set forth in claim 4 which includes, sealing said chambers one from another to form planar surfaces between said chambers.

* * * * *

UNITED STATES PATENT AND TRADEMARK OFFICE
CERTIFICATE OF CORRECTION

PATENT NO. : 4,753,241

DATED : June 28, 1988

INVENTOR(S) : PATRICK J. BRANNIGAN, GERALD L. PECKICH

It is certified that error appears in the above-identified patent and that said Letters Patent is hereby corrected as shown below: On the title page:

At [56] References Cited, change the second reference from "Paux" to --Poux--.

Column 13, line 36, change "purpose" to --purposes--.

Signed and Sealed this

Eighth Day of November, 1988

*Attest:*

DONALD J. QUIGG

*Attesting Officer* *Commissioner of Patents and Trademarks*